US005135531A

United States Patent [19]

Shiber

[11] Patent Number: 5,135,531

[45] Date of Patent: * Aug. 4, 1992

[54] GUIDED ATHERECTOMY SYSTEM

[75] Inventor: Samuel Shiber, Burlington, Mass.

[73] Assignee: Surgical Systems & Instruments, Inc., Mundelein, Ill.

[ * ] Notice: The portion of the term of this patent subsequent to Mar. 22, 2005 has been disclaimed.

[21] Appl. No.: 499,726

[22] Filed: Mar. 27, 1990

Related U.S. Application Data

[63] Continuation-in-part of Ser. No. 350,020, May 12, 1989, Pat. No. 4,979,939, which is a continuation-in-part of Ser. No. 326,967, Mar. 22, 1989, Pat. No. 4,957,482, Ser. No. 324,616, Mar. 16, 1989, Ser. No. 323,328, Mar. 13, 1989, and Ser. No. 332,497, Mar. 13, 1989, said Ser. No. 326,967, Ser. No. 324,616, Ser. No. 323,328, and Ser. No. 332,497, each is a continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, Ser. No. 205,479, Jun. 13, 1988, Pat. No. 4,883,458, and Ser. No. 225,880, Jul. 29, 1988, Pat. No. 4,842,579, said Ser. No. 78,042, Ser. No. 205,479, and Ser. No. 225,880, each is a continuation-in-part of Ser. No. 18,083, Feb. 24, 1987, Pat. No. 5,041,082, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.[5] .............................................. A61B 17/32

[52] U.S. Cl. .................................... 606/159; 606/170; 606/180; 604/22

[58] Field of Search ........................ 606/159, 170, 180; 604/98, 22

[56] References Cited

U.S. PATENT DOCUMENTS

| | | | |
|---|---|---|---|
| 4,517,977 | 5/1985 | Frost | 604/22 X |
| 4,589,412 | 5/1986 | Kensey | 604/22 X |
| 4,589,414 | 8/1986 | Yoshida et al. | 604/22 |
| 4,631,052 | 12/1986 | Kensey | 604/22 |
| 4,662,371 | 5/1987 | Whipple et al. | 604/22 |
| 4,678,459 | 7/1987 | Onik et al. | 604/22 |
| 4,754,755 | 7/1988 | Husted | 604/22 X |
| 4,790,813 | 12/1988 | Kensey | 604/22 |
| 4,857,046 | 8/1989 | Stevens et al. | 606/159 |
| 4,923,462 | 5/1990 | stevens | 604/159 |
| 4,944,727 | 7/1990 | McCoy | 604/95 |
| 4,946,466 | 8/1990 | Pinchuck et al. | 604/94 X |

*Primary Examiner*—Robert A. Hafer
*Assistant Examiner*—Kerry Owens
*Attorney, Agent, or Firm*—Samuel Shiber

[57] ABSTRACT

An atherectomy system for coring, ingesting and removing an obstruction material from within a patient's vessel having a flexible guide wire defining a void for holding obstruction material during the atherectomy process and for accurately guiding a flexible catheter in the vessel. Coupling means at the proximal end of the flexible catheter for coupling it to drive means.

47 Claims, 5 Drawing Sheets

161 13 140 160 170 12 12 24 23 22 25 24 21 71 170 160 17 71 140 71 73 72 74 25 17 10 27 31 34 33 39 28' 29 20 28 32 15 33 160 14 17 24 162 19

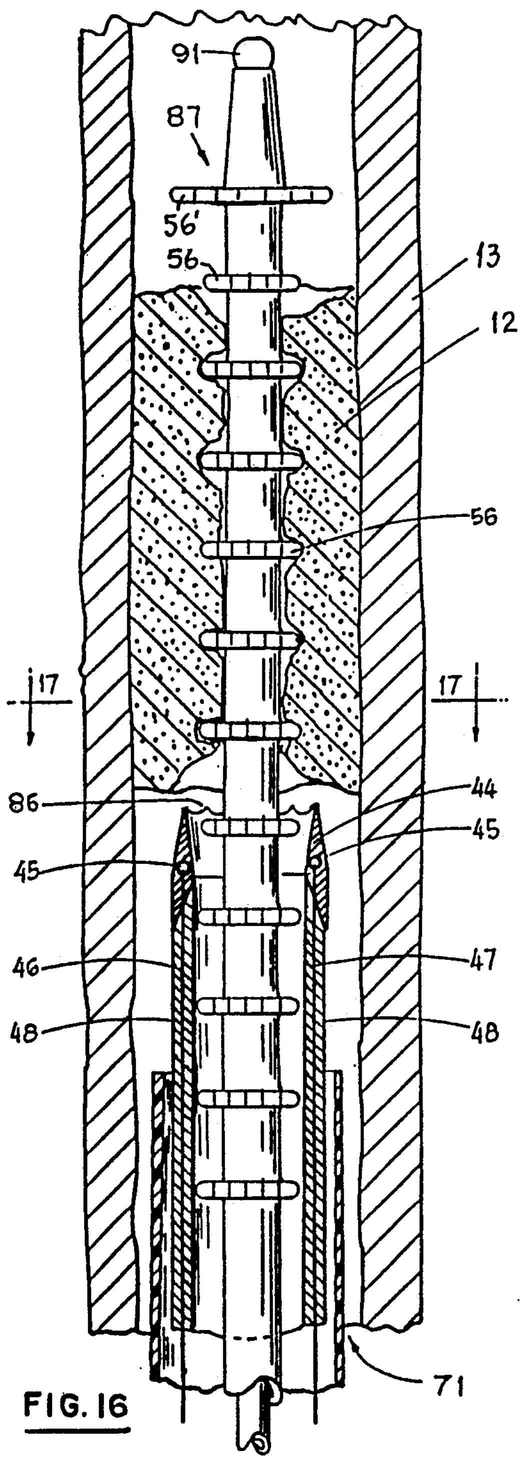
FIG. 16
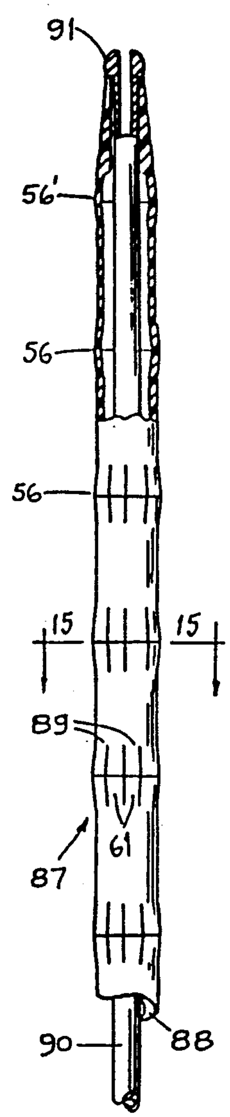
FIG. 14
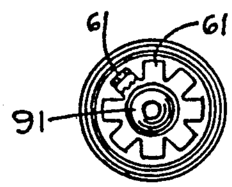
FIG. 17
FIG. 15

GUIDED ATHERECTOMY SYSTEM

CROSS REFERENCE TO OTHER APPLICATIONS

This application is a continuation in part (CIP) of application Ser. No. 07/350,020 now U.S. Pat. No. 4,979,939 filed May 12, 1989 which is a CIP of four applications: application Ser. No. 07/326,967 now U.S. Pat. No. 4,957,482 filed Mar. 22, 1989, application Ser. No. 07/324,616 filed Mar. 16, 1989, application Ser. No. 07/323,328 filed Mar. 13, 1989, and application Ser. No. 07/332,497 filed Mar. 13, 1989. These four applications are CIPs of application Ser. No. 07/286,509 filed Dec. 19, 1988 (now U.S. Pat. No. 4,894,051) which is a CIP of application Ser. No. 07/243,900 filed Sep. 13, 1988 (now U.S. Pat. No. 4,886,490), which is a CIP of three applications, application Ser. No. 07/078,042 filed Jul. 27, 1987 (now U.S. Pat. No. 4,819,634), application Ser. No. 07/205,479 filed Jun. 13, 1988 (now U.S. Pat. No. 4,883,458), and application Ser. No. 07/225,880 filed Jul. 29, 1988 (now U.S. Pat. No. 4,842,579). These three applications are CIPs of application Ser. No. 07/018,083 now U.S. Pat. No. 5,041,082 filed Feb. 24, 1987, which is a CIP of application Ser. No. 06/874,546 filed Jun. 16, 1986 (now U.S. Pat. No. 4,732,154) which is a CIP of application Ser. No. 06/609,846 filed May 14, 1984 (abandoned).

All the above applications are being incorporated herein by reference.

BACKGROUND AND OBJECTIVES OF THE INVENTION

With age a large percentage of the population develops atherosclerotic arterial obstructions resulting in diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by angioplasty which tends to injure the arterial wall, create a rough lumen and in substantial number of cases is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the present invention is to provide an atherectomy system having a flexible guide wire with a casing which positively guides a flexible catheter to and through an obstruction. The flexible guide wire defines a void or voids in which the obstruction material is positively held during the coring process. The process does not crack the vessel's wall and yields an enlarged smooth lumen.

Preferably, the system could be made in large and in small diameters, down to approximately 1 mm (millimeter) and a length of approximately a meter, to reach and enter small and remote arteries. The system's operation will preferably utilize the physician's existing skills such as: gaining access to the vessel, guide wire placement through the obstruction, angiographic evaluation of the obstruction, etc.

The above and other objectives of the invention will become apparent from the following discussion and the accompanying drawings.

BRIEF DESCRIPTION OF THE FIGURES

FIG. 5 ′ shows two optional blade configurations.

FIG. 14 shows the flexible guide wire used in the embodiment of FIG. 16 with barrier means in their contracted position.

FIG. 15 shows a cross sectioned view of the flexible guide wire shown in FIG. 14 along a line 15—15 marked on FIG. 14.

FIG. 16 shows a cross sectioned view of the distal end portion of an atherectomy system with a coring means in the form of a tubular-blade utilizing auxiliary energy, disposed over a flexible guide wire having expanded barrier means.

FIG. 17 shows a cross sectioned view of the system shown in FIG. 16 along a line 17—17 marked on FIG. 16.

DETAILED DESCRIPTION OF THE DRAWINGS

Figure 1:
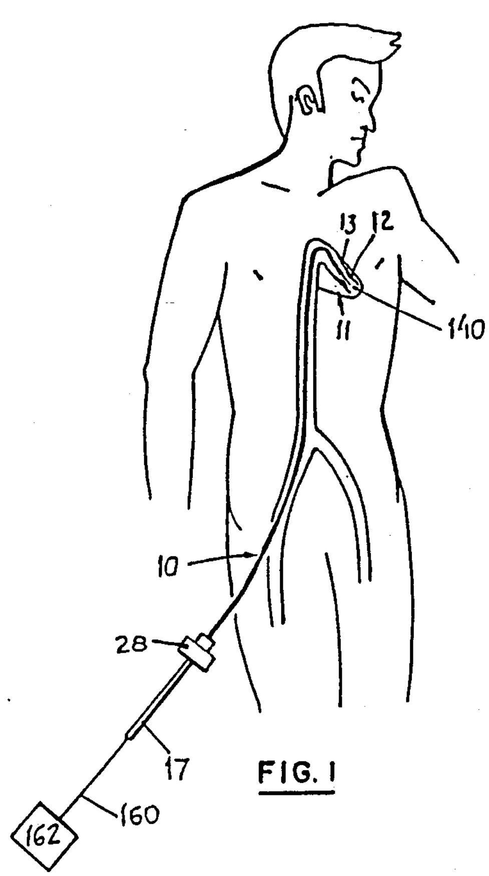
FIG. 1 generally shows an atherectomy system inserted at the groin area through the arterial system of a patient, into his obstructed coronary artery.

FIG. 1 generally shows an atherectomy system 10 inserted at the groin area through the skin, through a patient's arterial system, into a coronary vessel 13 serving the patient's heart 11.

Figure 2:
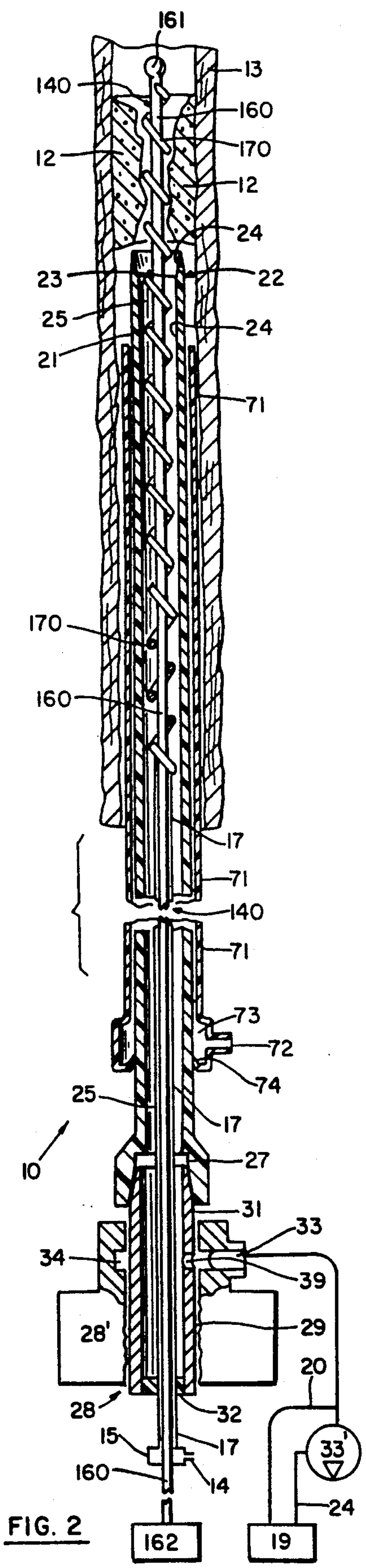
FIG. 2 shows a cross sectioned view of an atherectomy system with a flexible guide wire made of a flexible casing in the form of a helical wire attached to a proximal extension tube and a flexible pilot wire incorporating an ultrasound pod. The middle portion of the atherectomy system is removed due to space limitations on the drawing sheet.

FIG. 2 shows the atherectomy system 10 (similar parts will be indicated by same numbers throughout the FIGURES) for removing an obstruction 12 from within the patient's vessel 13. The atherectomy system comprises several elongated parts in a nested relationship, and their ends shall be referred to as "distal" meaning the end which goes into the vessel and "proximal" meaning the other end. Thus, "distal direction" or "distally" shall indicate a general direction from the proximal end to the distal end, and "proximal direction" or "proximally" shall refer to an opposite direction.

The atherectomy system comprises:

A flexible guide wire 140 insertable into the vessel.

A flexible catheter 21 slidable over the flexible guide wire, having a coring means in the form of a tubular blade 22 at its distal end, defining a continuous passage 25 around the flexible guide wire for ingesting the cored obstruction material.

The flexible guide wire is made of a thin walled stainless steel extension tube 17 or it can be made similarly to the catheters shown in my above mentioned U.S. Pat. No. 4,819,634. The extension tube 17 is attached to an auger shaped helical wire 170 which is slidably guided over the flexible pilot wire 160. Silicon oil or other bio-compatible lubricants may be disposed in the extension tube to ease the motion of the flexible pilot wire therein, while preventing blood from clotting inside the extension tube and interfering with this motion. A helical void is defined between the coils of the wire 170 for holding the obstruction material.

A nipple 14 is connected to the proximal end of the extension tube 17 through an annular chamber 15 which slidingly seals around the flexible pilot wire.

Figure 5:
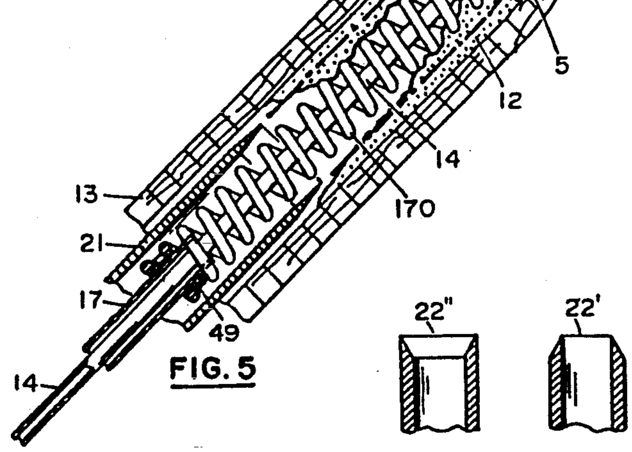
FIG. 5 shows the trajectory of the system in a cross sectioned, curved obstructed artery, when the coring process is done over a flexible guide wire having a casing over which the flexible catheter is accurately guided.
Figure 5:
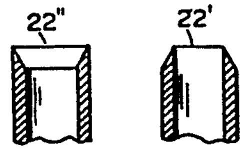

The flexible guide wire's section which extends distally into the vessel from the flexible catheter concentrically aligns the flexible catheter with the vessel and provides a lever arm which angularly aligns the flexible catheter with the vessel (also not FIG. 5).

When the flexible catheter's distal end 23 bears against the vessel's wall, it does so through a relatively large contact area, spreading the contact force and minimizing any trauma to the vessel.

The atherectomy system uses "mechanical energy" to advance and rotate the tubular blade and additional "auxiliary energy", emitted by the distal end portion of the atherectomy system, to soften a boundary layer of the obstruction material and ease in the coring process. The auxiliary energy can be in the form of, for example, heat, laser or ultrasound energy. Some of the auxiliary energy can be retrieved by a suitable transducer and processed to image the obstruction site in order to make the coring process safer and to assess the results of the procedure.

Coring the obstruction material is more efficient than pulverizing all of the obstruction material. To illustrate this point, when a tubular blade having a wall thickness of 0.25 mm cores an obstruction with an outside diameter of 5 mm and an inside diameter (lumen) of 1 mm the area of the boundary layer that the tubular blade has to pulverize is only a fifth of the obstruction's area and correspondingly one fifth of the volume.

Suction can be applied to the flexible catheter through a port 33 which communicates with a groove 34 defined by a motor's housing 28', which communicates with hole 39, which communicates with a hollow shaft 29, which communicates with the proximal end of the continuous passage 25. Preferably the suction is provided by a positive displacement pump 33' such as a piston pump or a peristalic pump which tends to self regulate the evacuation process: it limits the amount of blood removed through the flexible catheter to the volume that is positively displaced by the pump, when only free flowing blood is present in the continuous passage the negative pressure in the continuous passage automatically drops, as obstruction material enters the continuous passage the negative pressure automatically rises and pulls the cut material proximally. A feedback control 19 can be used to decrease the pumping rate of pump 33', through wiring 24 in response to sensing through a tube 20 that the negative pressure between the pump and the catheter is below a certain level. Preferably, the suction is synchronized with the coring action, or it is otherwise selectively controlled. These controls are designed to reduce the amount of blood removed from the patient during the procedure. The maximum level of negative pressure can be limited to prevent collapsing of the vessel wall. Coupling means at the proximal end of the flexible catheter in the form of a conical seat 27 couples it to a drive means in the form of a motor 28 having the hollow shaft 29 with a matching tapered end 31 and a seal 32 at its other end. The hollow shaft and seal are slidingly disposed around the flexible guide wire.

A pod 161 is used to emit auxiliary energy, which is sent by the base unit 162 through the flexible pilot wire, to the surrounding tissue, to soften the surrounding obstruction material, and to optionally retrieve signals in the form of returned auxiliary energy which is sent back to the base unit to be processed to form an image of the obstruction site. Laser energy can be used to obtain a topographical image and ultrasound energy to obtain a geological image. Relying on this information the physician can advance the pilot wire with a reduced risk of perforating the vessel's wall.

The helical wire 170 takes up the free play between the flexible pilot wire 160 and the flexible catheter 21 thereby concntrically aligning one with the other. A void defined between the helical wire's coils serves as a barrier, holding the obstruction material during the atherectomy and restraining the cored material from freely rotating around the flexible guidewire, and to the extent that the obstruction material is rotated by the flexible catheter this rotation is translated by the helical wire to urge the cored obstruction material proximally in the continuous passage. The helical wire can be inserted into a tight obstruction by rotating it, threading it into the obstruction. In the process of threading, the helical wire pulls itself across the obstruction and anchors itself in the obstruction material. When the flexible catheter is pushed forward in the vessel, the flexible guide wire can be pulled to offset the longitudinal force in the atherectomy system which tends to buckle the flexible catheter.

A flexible sleeve 71 in which the flexible catheter is disposed isolates the vessel's wall from the flexible catheter, and can be used to introduce the flexible catheter into the vessel and direct it to the obstruction's site. A nipple 72 is connected to the flexible sleeve through an annular chamber 73 equipped with a seal 74 which seals around the flexible catheter and communicates fluid entering the nipple 72 to move in the sleeve around the flexible catheter into the vessel.

Figure 3:
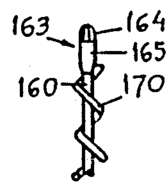
FIG. 3 shows a distal end portion of a flexible guide wire with an ultrasound pod having teeth on its distal end.
Figure 4:
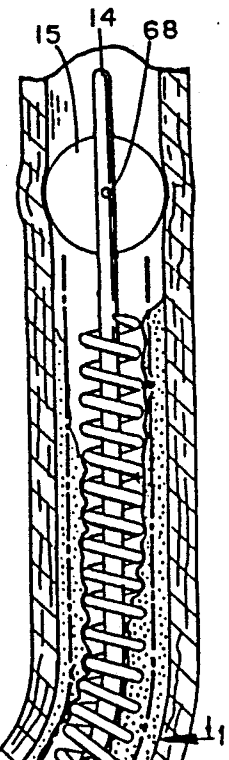
FIG. 4 shows a distal end portion of a flexible pilot wire with a similar pod to the one shown in FIG. 3, disposed in a deflecting sleeve.
Figure 4:
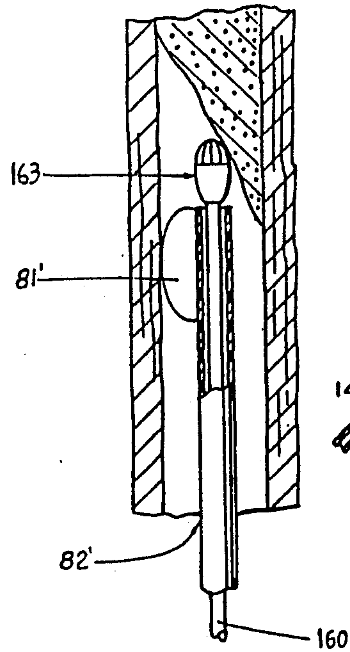

FIG. 3 shows a second embodiment of a pod 163 having protrusions 164 on its distal end for drilling and a mid section 165 for emitting and receiving auxiliary energy. The protrusions allow a physician to use the pod as a drill by rotating the pilot wire, enabling him to safely cross hard obstructions while knowing the pod's relative location to the vessel's wall. The protrusions may range in size from discrete teeth as shown in FIGS. 3 and 4 to microscopic protrusions which may be formed by bonding diamond particles to the pod's distal end. Auxiliary energy could be used to assist the pod in penetrating through the obstruction, with or without rotation thereof. The auxiliary energy which is emitted by the pod is transmitted to the adjacent obstruction material which eases the threading of the helical wire through the obstruction.

FIG. 4 shows a distal portion of a flexible pilot wire 160 disposed in a deflecting sleeve 82' having an inflatable chamber 81', for deflecting the trajectory of the flexible pilot wire in the vessel. The deflecting sleeve 82' and inflatable chamber 81' is a scaled down version of a deflecting sleeve 82 and an inflatable chamber 81 shown in FIGS. 20 and 21 and performs in the same manner. The deflecting sleeve can be sized to guide the pilot wire or to guide the whole flexible guide wire through the vessel.

FIG. 5 shows the trajectory of an atherectomy system in a cross sectioned, curved obstructed vessel, when the coring process is done over a hollow flexible pilot wire 14 and a casing made of a helical wire 170 attached by a brazing 49 to an extension tube 17. An optional inflatable chamber 15 is attached to the pilot wire and can be inflated or deflated through the hollow flexible pilot wire 14 which communicates fluid from its proximal end to an orifice 68. The inflatable chamber can be used to center the flexible pilot wire in the vessel, to cushion the contact between the flexible pilot wire and the vessel's wall as well as for anchoring it to the vessel's wall. If the inflatable chamber is asymmetric it can also be used to selectively bias the position of the flexible pilot wire in the vessel.

FIG. 5' shows two optional blade configurations that will be discussed later on.

Figure 6:
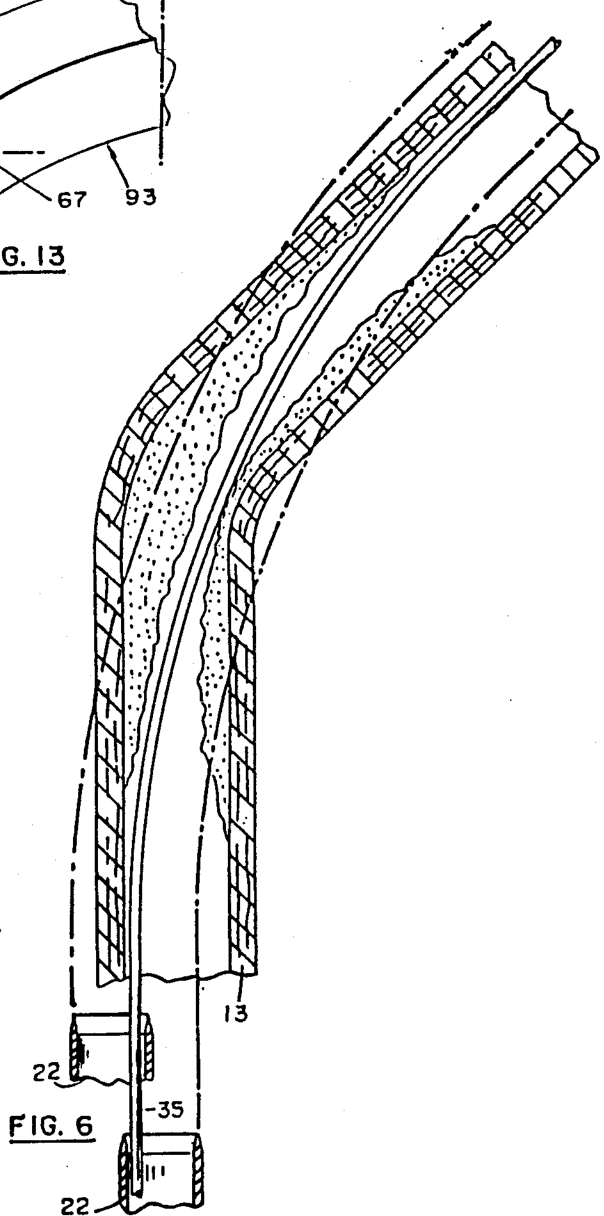
FIG. 6 shows the possible range of trajectories of the system in a cross sectioned, curved obstructed artery, when the coring process is done over a standard flexible guide wire.

FIG. 6 shows the range of possible trajectories of the system in a cross sectioned, curved obstructed vessel, when the coring process is done directly over a standard flexible guide wire 35.

Figure 7:
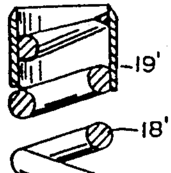
FIGS. 7 and 7′ shows an enlarged, partially sectioned view of the distal end section of a helical wire where the distal entry to the void defined between the coils is partially closed by a short tube.

FIG. 7 shows an enlarged, partially sectioned view of the distal end section of a casing in the form of a helical wire 18 where the distal entry to the void defined between the coils is partially closed by a thin gate in the form of a short tube 19, preferably made from radio opaque material (for example an alloy comprising gold and/or platinum), attached to the internal diameter of the casing. The helical wire is made of a tube with a lumen 41 through which auxiliary energy can be conveyed and emitted at the distal end of the helical wire to ease its threading into the obstruction material.

Figure 8:
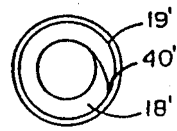
FIGS. 8 and 8′ show end views of the helical wire shown in FIG. 7 and 7′, respectively.

FIG. 8 shows a distal end view of the casing shown in FIG. 7 in the form of a helical wire 18 having a pointed distal end 40 to ease penetration into the obstruction material.

FIG. 7' shows an enlarged, partially sectioned view of the distal end section of a casing in the form of a helical wire 18' where the distal entry to the void defined between the coils is partially closed by a thin gate in the form of a short tube 19', preferably made from radio opaque material, attached to the outside diameter of the casing.

FIG. 8' shows a distal end view of the casing shown in FIG. 7' in the form of a helical wire 18' having a pointed distal end 40' to cut and ease penetration into the obstruction material.

Figure 9:
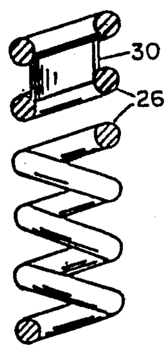
FIG. 9 shows an enlarged, partially sectioned view of the distal end section of a helical wire where the distal entry to the helical void defined between the coils is partially closed by a tube section.
Figure 7:
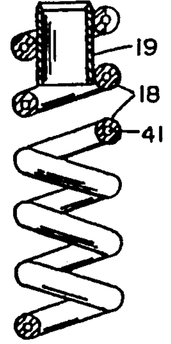

FIG. 9 shows an enlarged, partially sectioned view of the distal end section of a casing in the form of a helical wire 26 where the distal entry to the void defined between the coils is partially closed by a thin gate in the form of a tube section 30, preferably made from radio opaque material, attached between the coils of the helical wire, adjacent to the internal diameter of the casing.

Figure 10:
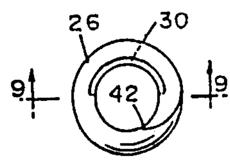
FIG. 10 shows an end view of the helical wire shown in FIG. 9.
Figure 8:
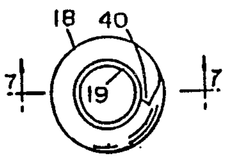

FIG. 10 shows a distal end view of the casing shown in FIG. 9 in the form of a helical wire 26 having a pointed distal end 42 to ease penetration of the obstruction material. As the helical wire 26 is rotated and advanced around a flexible pilot wire the point 42 remains adjacent to the flexible pilot wire. If the flexible pilot wire is disposed against the arterial wall, as the helical wire is advanced and rotated, its inclined leading edge gently separates the arterial wall from the flexible pilot wire and centers it in the vessel. Optionally the point 42 can be moved away from the flexible pilot wire, as shown in FIG. 8, which makes the pointed helical wire thread more aggressively through the obstruction material while reducing its ability to separate the arterial wall from the flexible pilot wire as discussed above.

Figure 11:
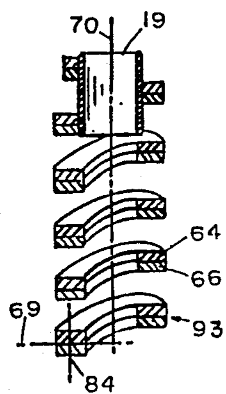
FIG. 11 shows an enlarged, sectioned view of the distal end section of a helical wire made of two flat layers, where the distal entry to the helical void defined between the coils is partially closed by a short tube.

FIG. 11 shows an enlarged, sectioned view of the distal end section of a casing in the form of a helical wire 93 made of two flat layers 64 and 66, where the distal entry to the void defined between the coils is partially closed by a thin gate in the form of a short tube 19 attached to the internal diameter of the casing. The multi layer construction decreases the cross section modulus of the helical wire around a neutral axis 69 which is perpendicular to the main axis 70, as compared with a non-layered construction, but it has minimal effect on the cross section modulus around a neutral axis 84 which is parallel to the main axis 70.

Figure 12:
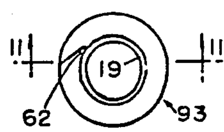
FIG. 12 shows an end view of the helical wire shown in FIG. 11.

FIG. 12 shows a distal end view of the casing shown in FIG. 11 in the form of a helical wire having a pointed distal end 62 for the purpose discussed above in conjunction with FIG. 10.

Figure 13:
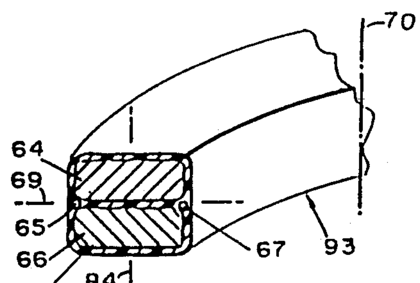
FIG. 13 shows a further enlargement of the cross section of the helical wire of FIG. 12.

FIG. 13 shows a further enlargement of the cross section of the helical wire of FIG. 12. The layers 64 and 66 are encapsulated in a plastic material 85 which holds them together and makes them thread through the obstruction material in unison, but is sufficiently flexible to allow their cross section modulus to be that of two separate layers. Auxiliary energy conduits 65 and 67, are also encapsulated by the plastic material along side the layers of the wire. Preferably, the plastic material has a slippery outer surface to ease its insertion through the vessel and its threading through the obstruction material.

FIG. 14 shows a flexible guide wire 87 having a hollow pilot wire 90 and a casing in the form of thin jacket 88 with arrays of slits 89 which define collapsible and expandable ribs 61. The jacket is slidable over the flexible pilot wire 90, up to an enlarged rounded distal end 91. Under the compressive force which is generated by pushing the proximal end of the jacket while pulling the proximal end of the flexible pilot wire, the ribs fold and expand to form barriers 56, as shown in FIGS. 16 and 17, and at this position they define a void (the term "void" as used in conjunction to this application shall mean the gaps defined between barriers 56, collectively, or it may refer to a single continuous gap, as in previous embodiments) which holds the surrounding obstruction material and counters its distal movement during the atherectomy. The diameter of the expanded top barrier element 56' can be made larger than the inner diameter of the flexible catheter to block a larger cross sectional area of the vessel, whereas the other barrier elements are made to fit inside the flexible catheter which they slidably support.

The hollow pilot wire 90 can be used as a conduit for delivering fluids to the obstruction site and beyond, such as: radio opaque fluid to assist in fluoroscopic imaging of the vessel, oxygen rich fluid for providing nourishment to deprived cells during the procedure, or fluid for irrigating the work site.

FIG. 15 shows a cross sectioned view of the flexible guide wire shown in FIG. 14.

FIG. 16 shows a distal end portion of an atherectomy system having a coring means in the form of a tubular blade 44. The tubular blade has teeth 86 and a ring shaped element 45 in the blade, to which auxiliary energy is conveyed by means of two flexible conduits 46 and 47 located in a wall of a flexible catheter 48. The tubular blade emits auxiliary energy to the surrounding obstruction material. The emitted energy may have several forms which assist the blade in coring the obstruction material. If the auxiliary energy is thermal the ring can be a resistive-element to which the conduits carry electrical current or the ring can be made to absorb laser energy and then the conduits would be fiberoptic bundles. Optionally, the tubular blade can be made from semi-transparent or transparent material, and part or all of the laser energy can be transmitted directly to the obstruction material. If the emitted energy is ultrasound energy the ring can be a piezoelectric transducer to which the conduits carry electrical current.

The auxiliary energy delivered to the tubular blade eases the coring process by softening the boundary layer, and since the obstruction material is positively held in the void defined by the flexible guide wire 87 it may be possible to core the obstruction by pushing the catheter without rotating it, especially if there is an anatomical reason not to impart torque onto the vessel for example, when working in a graft that is poorly attached to the surrounding tissue. However, coring by rotation is preferable because it is more effective and the relative rotational motion between the vessel and the flexible catheter which entails overcoming the frictional force between them, eases the advancement of the flexible catheter in the vessel. The relative rotational motion between the flexible catheter to the obstruction material, which also entails overcoming the frictional force between them, eases the proximal movement of the obstruction material in the flexible catheter (because overcoming the frictional forces between two bodies, due to a relative motion between them in one direction, minimizes the frictional resistance to a relative motion between them in a perpendicular direction).

FIG. 17 shows a partially cross sectioned view of the system shown in FIG. 16.

Figure 18:
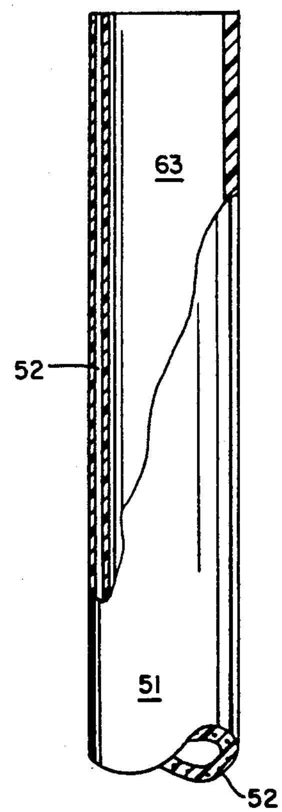
FIG. 18 shows a cross sectioned view of an atherectomy system where the coring means utilizes a radiation emitting device (the flexible guide wire is omitted).

FIG. 18 shows a flexible cathether 51 with a coring means utilizing auxiliary energy, preferably in the form of laser energy carried by optical fibers 52 and emitted through their distal ends. The auxiliary energy cores the obstruction by ablating a narrow boundary layer in it and the continuous passage 63 ingests the cored obstruction material as in previous embodiments. Similarly to the tubular-blade, the laser based coring means is efficient and uses less energy in comparison to other laser based systems which ablate all the material of the obstruction.

Optionally, the emitted laser energy can be directed in a slightly outwardly inclined direction as shown in FIG. 18, so that a wider boundary layer of material would be ablated to make the diameter 94 of the recanalized vessel larger than the diameter 95 of the flexible catheter 51 and larger than the puncture wound that is needed to introduce the flexible catheter into the vessel, while the center part of the obstruction can still be cored unpulverized.

The flexible catheter 51 can be disposed in any of the sleeves shown in connection to the embodiments of the present invention. By using a sleeve equipped with a toroidal chamber to block blood flow as explained above and by introducing fluid to the obstruction site, for example saline solution, through the sleeve or the flexible catheter, a working medium of choice can be created to suite a specific type of radiation and to allow visual or spectroscopic analysis of the vessel's lumen.

As previously discussed, the auxiliary energy may enable the physician to core the obstruction material by pushing the flexible catheter with or without rotating it.

Figure 19:
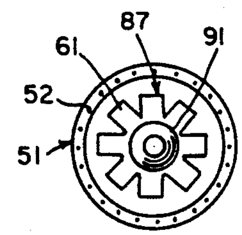
FIG. 19 shows a distal end view of the system shown in FIG. 18.

FIG. 19 shows a distal end view of the flexible catheter shown in FIG. 18 together with the flexible guide wire 87.

Figure 20:
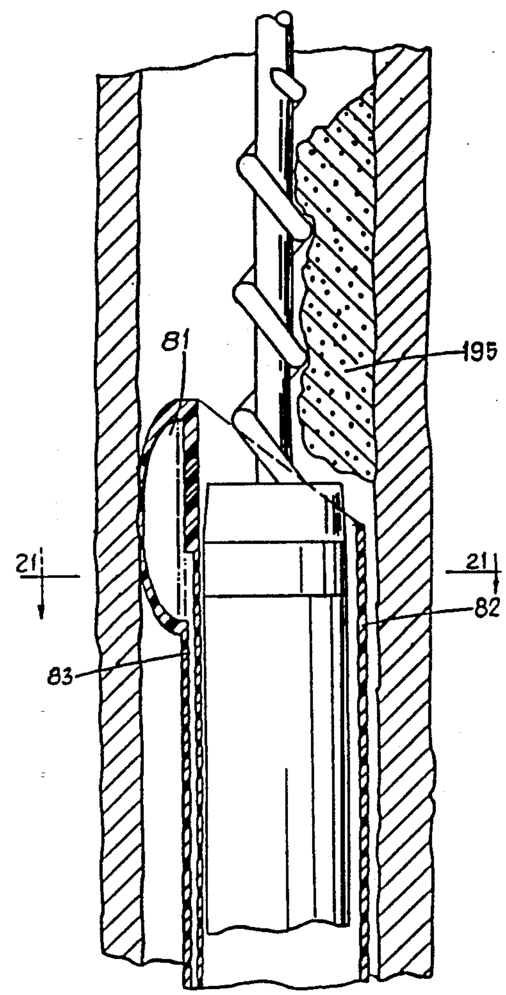
FIG. 20 shows a partially cross sectioned view of an inflatable chamber located at the distal end of the flexible sleeve.
Figure 21:
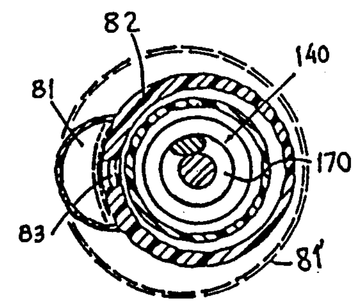
FIG. 21 shows a cross sectioned view of the system shown in FIG. 20, along a line 21—21 marked on FIG. 20.

FIGS. 20 and 21 show a biasing means in the form of an asymmetrical inflatable chamber 81 formed at the distal end of a flexible deflecting sleeve 82 which, when inflated, through a channel 83 formed in the sleeve's wall, bears against the vessel's wall, as shown in solid lines, eccentrically biasing the flexible sleeve and the coring means towards an accentric obstruction 195. When deflated, as shown by phantom lines, the chamber conforms to the sleeve to minimize interference with its insertion into the vessel. Alternatively the chamber can be shaped as an asymmetrical toroidal inflatable chamber 81' as shown in FIG. 21 by interrupted lines. This chamber, when inflated, establishes peripheral contact with the vessel's wall and thereby blocks blood flow between the sleeve and the vessel's wall, as well as eccentrically biasing the sleeve (it can be understood that a symmetrical toroidal chamber can be provided for the purpose of blocking the flow around the sleeve while centering the biasing sleeve). Any of the above mentioned chambers can also be inserted into the lumen that has been cored by the coring means, to be inflated therein with sufficient pressure, and to further widen the lumen, however, such a procedure may introduce the drawbacks of angioplasty.

Figure 22:
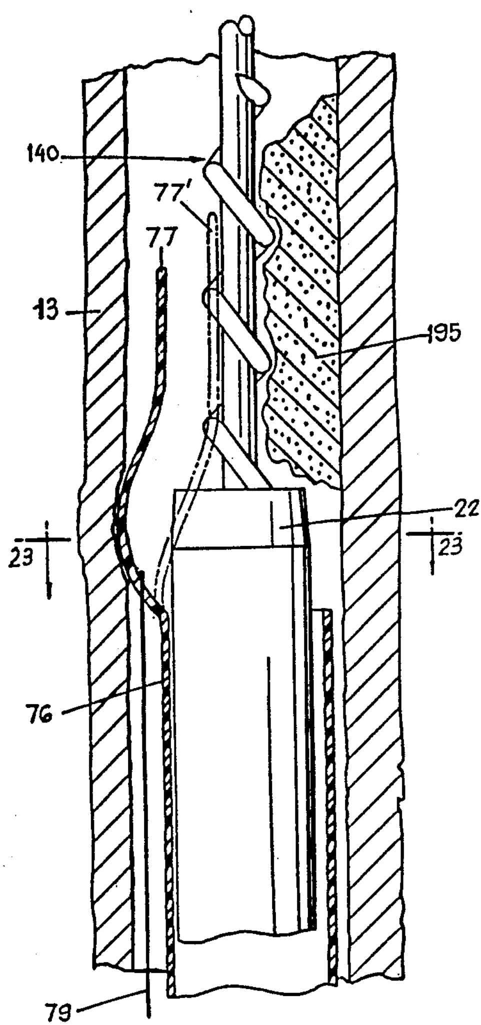
FIG. 22 shows a partially cross sectioned view of an atherectomy system with a flexible sleeve having a selectively actuatable tongue at its distal end.
Figure 23:
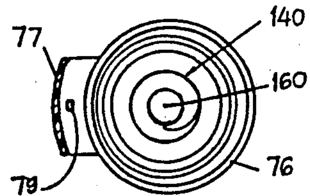
FIG. 23 shows a partially cross sectioned view of the system shown in FIG. 22 along the line 23—23 marked on FIG. 22.

FIGS. 22 and 23 show an atherectomy system where a flexible sleeve 76 has a tongue 77 which can be used when coring an eccentric obstruction 195. In such a case the tongue can be inserted opposite of the obstruction to protect the vessel wall and bias the trajectory of the coring means into the obstruction. The tongue can be energized against the vessel's wall by tensioning a flexible rope 79, moving the tongue from its relaxed position which is shown by a phantom line in FIG. 22 and marked 77' to the position shown in solid lines and marked 77.

OPERATION

FIG. 5 illustrates the atherectomy process. First a portion of the flexible pilot wire 14 is inserted into the curved vessel, and assumes the vessel's geometry. Then the casing in the form of the helical wire 170 is inserted over the flexible pilot wire, preferably by threading it through the obstruction. The flexible pilot wire acts as a lever arm 3 to angularly align and safely guide the advancing helical wire 170 through the curved vessel. Without the lever arm's guidance the advancing helical wire would contact the vessel's wall at approximately a point 1 and exert a large concentrated compressive force until the bending moment which equals the product of that force multiplied by the short lever arm 2 would be sufficient to bend the helical wire around an axis 5 perpendicular to the plane of curvature of the vessel (and therefor shown perpendicular to the drawing sheet by a checkered circle). In comparison, with the flexible pilot wire's longer lever arm 3 the required force is smaller and it is spread by the lever arm over a longer and larger contact area of the vessel's wall.

Once the helical wire is in place it reinforces the obstruction material and firmly holds it in place, preparatory to coring it. At this point the physician has an opportunity to, fluoroscopically or by the use of auxiliary energy imaging, assess the position of the flexible guide wire in the vessel. The flexible guide wire's portion that has been inserted through the obstruction material now serves to concentrically align the flexible catheter with the vessel and also serves as a lever arm which angularly aligns the flexible catheter with the vessel during the atherectomy. The angular alignment of the flexible catheter by the flexible guide wire is very similar to the alignment of the helical wire over the fexible pilot wire; the flexible catheter is inserted over the flexible guide wire which acts as a lever arm 4 to angularly align and safely guide the advancing flexible catheter. Without the lever arm's guidance the advancing coring means would contact the vessel's wall at approximately a point 1 and exert a large concentrated compressive force until the bending moment which equals the product of that force multiplied by the short lever arm 2 would be sufficient to bend the flexible catheter around the axis 5, however such a compressive force will likely cause the coring means to cut and perforate the vessel. In comparison, with the flexible guide wire's longer lever arm the required force is smaller and it is spread by the lever arm over a longer and larger area of the vessel's wall. Phantom lines mark the anticipated trajectory of the coring means when it is accurately guided in the vessel as discussed.

FIG. 5' shows two optional blade configurations. The right hand configuration shows a blade 21' where the diameter of the sharp edge is on internal diameter of the blade and is connected by a taper to the external diameter. The taper acts to distance the sharp edge from the arterial wall making it a safer configuration preferred for working in a torturous vessel. If the blade is smooth the taper does not pulverize the boundary layer but tends to push it outwardly.

The left hand configuration 22'' shows a blade where the diameter of the sharp edge is on the outside diameter of the blade and an inverted taper connects it to the internal diameter. If the blade is smooth the inverted taper does not pulverize the boundary layer but tends to push it inwardly and core it, however, with this configuration there is a higher probability of injuring the arterial wall. Alternatively, the sharp edge can be formed between the internal and outside diameters, as shown in FIGS. 5 and 6, to combine in part the characteristics of both blade configurations.

FIG. 6 illustrates the potential risk of guiding the coring process over a standard flexible guide wire directly. As the tubular blade advances along the flexible guide-wire its trajectory can vary angularly and sideways in the range defined between the two phantom lines, and any material disposed between the phantom lines, including large segments of the vessel's wall, might be cored.

The process for removing an obstruction from a vessel with an atherectomy system comprises the following steps:

a. Inserting into a vessel, into an obstruction, a flexible pilot wire. The flexible pilot wire can be constructed like a standard flexible guide wire, or it can be equipped with various means to assist the physician in inserting it and guiding it through the arterial system and the obstruction.

b. Inserting into a vessel, into an obstruction, over the flexible pilot-wire a flexible casing having a void for holding the obstruction material (the flexible pilot wire and casing can be pre-assembled before insertion or permanently affixed one to the other, in which case the insertion of the flexible guide wire assembly into the vessel is done in a single step which replaces the above two steps).

c. Advancing over the casing a coring means located at a distal end of a flexible catheter, coring and ingesting the obstruction material which is held in place by the void. Concentric and angular alignment is provided by the flexible guide wire to the advancing coring means.

d. Suction, which is preferably provided by a positive displacement pump means, may be used to assist the cored obstruction material to move proximally in the flexible catheter.

The sequence of inserting the system's components into the vessel may be varied. Steps may be combined or added to streamline or improve the process, respectively, and in order to customize the procedure to the individual characteristics of the obstruction and its location and to the working preferences of the medical staff. For example, the system may be introduced percutaneously (that is through the skin) or intra-operatively (that is when the vessel is surgically exposed for accessing vessel), a standard guiding catheter, which is either straight or pre-formed or has a selectively controlled curve, may be used as a sleeve and inserted into the vessel to assist in positioning the system's components in the obstruction site.

The preferred mode of operating an atherectomy system having an auger shaped flexible guide wire is to first thread the flexible guide wire by rotating it in one direction and advancing it across the obstruction, like a screw in a cork, and then hold the flexible guide wire in place while advancing and rotating the flexible catheter in an opposite direction, over the stationary flexible guide wire. It is also possible to continue and rotate the flexible guide wire to increase the auger's proximal conveyance action, especially when coring an obstruction with a slurry like consistency such as fresh blood clots.

An atherectomy system can be manufactured in different diameters and lengths depending on the size and site of vessel that it is intended for and on whether the system is to be used percutaneously or intra-operatively.

It can be noted from the FIGURES that the basic components of the atherectomy system can have several optional features and design variations. The flexible catheter can be made from plastic or metal or from a combination thereof and the coring means can utilize mechanical energy and/or auxiliary energy. The flexible guide wire can be equipped with various types of casing designs, some of which are affixed to the pilot wire and others that are slidable thereon. The sleeve can be equipped with mechanical or hydraulic biasing means. By combining a flexible catheter with certain features, a flexible guide wire with certain features and a sleeve with certain added features a variety of customized atherectomy systems can be made. This increases the user's ability to match the system's characteristics with the specific disease condition that is being treated, which is helpful, since the clinical characteristics of arterial atherosclerotic obstructions vary in their topography, geology and accessibility from one patient to another.

The above and other modifications and substitutions can be made in the system and in its operation without departing from the spirit of the invention or the scope of the following claims.

I claim:

1. An atherectomy system for removing an obstruction material from within a patient's vessel, comprising in combination:

a flexible guide wire insertable into said vessel, said flexible guide wire defining a void for holding the obstruction material, a flexible catheter with a coring means at its distal end having a continuous passage for ingesting the cored obstruction material, said flexible catheter being guided by and slidableover said flexible guide wire, coupling means at a proximal end of said flexible catheter for connecting said flexible catheter to drive means.

2. An atherectomy system as in claim 1, said coring means being a tubular blade.

3. An atherectomy system as in claim 1, said coring means being a tubular blade having at least one tooth.

4. An atherectomy system as in claim 1, said coring means utilizing auxiliary energy.

5. An atherectomy system as in claim 1, said coring means being a tubular blade utilizing an auxiliary energy to assist in coring the obstruction material.

6. An atherectomy system as in claim 1, having a flexible sleeve in which said flexible catheter is disposed.

7. An atherectomy system as in claim 6, said flexible sleeve having a means for biasing it in said vessel.

8. An atherectomy system as in claim 7, said biasing means comprise an inflatable chamber formed at said distal end of said flexible sleeve.

9. An atherectomy system as in claim 7, said flexible sleeve having a tongue at its distal end for biasing said flexible sleeve in said vessel.

10. An atherectomy system as in claim 9, said tongue being selectively actuatable.

11. An atherectomy system as in claim 6, wherein fluid transmitting means to said vessel are connected to said flexible sleeve.

12. An atherectomy system as in claim 1, wherein suction is applied to pull the cored obstruction material proximally in said continuous passage.

13. An atherectomy system as in claim 12, wherein said suction is provided by a positive displacement pump means.

14. An atherectomy system as in claim 1, wherein a portion of said flexible guide-wire is inserted distally to said flexible catheter, into said vessel, concentrically aligns said flexible catheter with said vessel.

15. An atherectomy system as in claim 1, wherein a portion of said flexible guide-wire which extends distally from said flexible catheter into said vessel provides a lever arm which angularly aligns said flexible catheter with said vessel.

16. An atherectomy system as in claim 1, wherein at least a portion of said flexible guide wire is shaped as an auger.

17. An atherectomy system as in claim 16, said auger comprising a helical wire made of at least two layers, decreasing its cross section modulus around a neutral axis perpendicular to the auger's main axis.

18. An atherectomy system as in claim 1, wherein said flexible guide wire comprises a flexible pilot wire and a flexible casing slidable thereon, said flexible casing defines a void for holding the obstruction material.

19. An atherectomy system as in claim 18, said flexible pilot wire has an auxiliary energy pod at its distal portion.

20. An atherectomy system as in claim 19 wherein said auxiliary energy is emitted by said pilot wire to assist said helical wire in crossing the obstruction material.

21. An atherectomy system as in claim 18, said flexible pilot wire being a tube.

22. An atherectomy system as in claim 18, a portion of said flexible pilot wire is inserted distally to said flexible casing, into said vessel, and provides a lever arm to angularly align said flexible casing with said vessel.

23. An atherectomy system as in claim 18, at least a portion of said flexible casing being a helical wire.

24. An atherectomy system as in claim 23, said helical wire's distal end is closed with a thin gate.

25. An atherectomy system as in claim 24; said gate being a short tube attached to the distal end of said helical wire.

26. An atherectomy system as in claim 24, said gate being a tube section attached to the distal end of said helical wire.

27. An atherectomy system as in claim 23, wherein said helical wire emits auxiliary energy through its distal end.

28. An atherectomy system as in claim 23, said helical wire is made of a wire having a decreased cross section modulus around a neutral axis perpendicular to the helical wire's main axis.

29. An atherectomy system as in claim 28, said helical wire made of at least two layers, decreasing said helical wire's cross section modulus around a neutral axis perpendicular to the helical wire's main axis.

30. An atherectomy system as in claim 1, said flexible guide wire having a radially protruding barrier means.

31. An atherectomy system as in claim 30, wherein said barrier means can be selectively expanded.

32. An atherectomy system as in claim 1, said flexible guide wire having a pod at its distal portion for emitting and receiving auxiliary energy.

33. An atherectomy system as in claim 32, said distal end of said flexible guide wire having means to drill through the obstruction material.

34. An atherectomy system as in claim 33, wherein said drilling means comprise sharp protrusions.

35. An atherectomy system as in claim 33, wherein said drilling means utilize auxiliary energy.

36. An atherectomy system as in claim 1, having biasing means to deflect the trajectory of said flexible guide wire in said vessel.

37. An atherectomy system as in claim 36, said biasing means comprising a selectively inflatable asymmetrical chamber formed at said distal end of said flexible sleeve.

38. A process for removing an obstruction from a vessel with an atherectomy system, comprising the following steps:

inserting into a vessel, into an obstruction, a flexible guide wire, holding the obstruction material with the flexible guide wire, advancing over the flexible guide wire a coring means located at a distal end of a flexible catheter, advancing the coring means into the obstruction and coring the obstruction while the coring means is guided in and aligned with the vessel by the flexible guide wire.

39. A process as in claim 38, wherein the insertion of the flexible guide wire into the vessel is assisted by signals generated by auxiliary energy.

40. A process as in claim 38, wherein a radio-opaque fluid is injected through the flexible guide wire to facilitate fluoroscopic imaging of the vessel.

41. A process as in claim 38, wherein suction is used to assist in proximally moving the cored obstruction material in the flexible catheter.

42. A process as in claim 41, wherein the suction is provided by a positive displacement pump means.

43. A process for removing an obstruction from a vessel with an atherectomy system, comprising the following steps:

inserting into a vessel, into an obstruction, a flexible pilot wire, inserting into a vessel, into an obstruction, over the flexible pilot wire a flexible casing defining a void for holding the obstruction material, advancing over the flexible casing a coring means located at a distal end of a flexible catheter, advancing the coring means into the obstruction and coring the obstruction while the coring means is guided in and aligned with the vessel by the flexible casing.

44. A process as in claim 43, wherein the insertion of the flexible pilot wire into the vessel is assisted by signals generated by auxiliary energy.

45. A process as in claim 43, wherein a radio-opaque fluid is injected through the flexible pilot wire to facilitate fluoroscopic imaging of the vessel.

46. A process as in claim 43, wherein suction is used to assist in proximally moving the cored obstruction material in the flexible catheter.

47. A process as in claim 46, wherein the suction is provided by a positive displacement pump means.

* * * * *